United States Patent [19]

Lines et al.

[11] 4,157,346

[45] Jun. 5, 1979

[54] CATALYTIC EPOXIDATION OF ALKYLENE COMPOUNDS

[75] Inventors: Ellwood L. Lines, New Haven; Robert J. Fairbrother, Cheshire; John A. Herbst, Madison, all of Conn.

[73] Assignee: Olin Corporation, New Haven, Conn.

[21] Appl. No.: 891,869

[22] Filed: Mar. 30, 1978

Related U.S. Application Data

[63] Continuation of Ser. No. 734,588, Oct. 21, 1976, abandoned, which is a continuation-in-part of Ser. No. 591,214, Jun. 27, 1975, abandoned.

[51] Int. Cl.$^2$ ............................................. C07D 301/12
[52] U.S. Cl. ........................... 260/348.31; 260/348.29
[58] Field of Search ..................................... 260/348.31

[56] References Cited

U.S. PATENT DOCUMENTS

| 3,122,569 | 2/1964 | Kaman | 260/348.31 |
|---|---|---|---|
| 3,489,775 | 1/1970 | Seree de Roch et al. | 260/348.31 |
| 3,597,459 | 8/1971 | Mimoun et al. | 260/429 |
| 3,668,227 | 6/1972 | Matucci et al. | 260/429 J |
| 3,778,451 | 12/1973 | Poite | 260/348.31 |
| 3,956,180 | 5/1976 | Cavitt | 252/431 R |

*Primary Examiner*—Norma S. Milestone
*Attorney, Agent, or Firm*—Robert J. Feltovic; Thomas P. O'Day

[57] ABSTRACT

An epoxidation method is described wherein an alkylene compound is reacted with a peroxidic compound, e.g., $H_2O_2$, in the presence of an improved molybdenum catalyst which is prepared by a selective reaction involving an oxygen-containing molybdenum compound, an amine, and an alkylene glycol.

10 Claims, No Drawings

CATALYTIC EPOXIDATION OF ALKYLENE COMPOUNDS

This is a continuation of application Ser. No. 734,588 filed Oct. 21, 1976, which in turn is a continuation-in-part of co-pending application Ser. No. 591,214, filed June 27, 1975.

The present invention relates to an improvement in the preparation of alkylene oxides. More particularly, the invention is directed to a method of epoxidizing alkylene compounds in the presence of a select molybdenum catalyst.

Various alkylene oxides have been produced by a variety of methods including the well-known chlorohydrin technique, the direct oxidation technique, and the epoxidation or indirect oxidation technique wherein alkylene is reacted with a peroxidic compound in the presence of an epoxidation catalyst. In connection with the latter technique, certain molybdenum compounds have been disclosed as being effective epoxidation catalysts. See for example U.S. Pat. No. 3,778,451 to Poite, No. 3,597,459 to Mimoun et al and No. 3,489,775 to de Roch et al.

Further in the prior art relating to molybdenum compounds, U.S. Pat. No. 3,285,942 to Price et al discloses certain products which are based on a reaction of molybdenum oxides with glycols in the presence of a nitrogenous compound. This reaction is carried out using such specified relative proportions of reactants as to yield products which are oxidation inhibitors rather than oxidation promoters.

Now an improvement has been found in the catalytic epoxidation of alkylene compounds. The improvement is based on the discovery of a new and improved group of molybdenum catalysts. According to the invention, these catalysts are prepared by a selective reaction, the details of which are provided hereinbelow, involving an oxygen-containing molybdenum compound, an amine and an alkylene glycol. Due to their high solubility in the epoxidation medium and their improved catalytic effect, these catalysts are used to advantage, according to the invention, in promoting the epoxidation of alkylene compounds.

In the method of the present invention, various organic oxides (epoxides) are produced by indirect oxidation in which a peroxidic compound is employed as the oxygen contributor. Alkylene compounds characterized by an olefinic unsaturation, i.e., having the functional group $>C=C<$, are oxidized to obtain the corresponding alkylene oxide. The term "alkylene" is used herein to include both substituted and unsubstituted compounds and encompasses any organic compound having an olefinic bond which may be oxidized with hydrogen peroxide in the presence of a metal compound catalyst. Among the alkylenes which may be oxidized by the method of the present invention are ethylenic hydrocarbons having, for example, 2 to 10 carbon atoms, such as ethylene, propylene, butene, hexene, etc., as well as polyethylenic hydrocarbons, such as butadiene or isoprene, and cyclic compounds such as cyclohexene or styrene. Additionally, substituted compounds such as ethylenic alcohols, e.g., allyl alcohol, ethylenic halides, e.g., allyl chloride, as well as unsaturated oils and fats may be oxidized by the method of the present invention. Particularly preferred alkylenes for use according to the invention are the lower alkylenes, e.g., ethylene, propylene and butylene, propylene being most preferred.

The peroxidic compound may be an organic peroxide, e.g., one having 1 to about 30, preferably about 3 to about 15, carbon atoms; or it may be an inorganic peroxide. Among the organic peroxidic compounds which may be used are the hydroperoxides of hydrocarbons, alcohols, esters, aldehydes and acyl moieties. Among the hydrocarbon hydroperoxides are those of linear and cyclic aliphatic hydrocarbons and alkyl aromatic hydrocarbons. Specific examples of these are cyclohexene hydroperoxide, tertiarybutyl hydroperoxide, methyl-4-pentene-2-hydroperoxide, methyl-2-pentene-2-hydroperoxide, cyclohexane hydroperoxide, cumene hydroperoxide, and ethyl benzene hydroperoxide.

As aliphatic hydroperoxides, there can even be employed polyolefinic hydroperoxides, such as, for example, polybutadiene hydroperoxide, or polyisoprene hydroperoxide. As specific examples of alcohol hydroperoxides, there are included, among others, the following: cyclohexanol hydroperoxide, methylphenyl carbynol hydroperoxide, and benzohydrol hydroperoxide.

Acyl hydroperoxides are very common epoxidation agents particularly the organic peracids, such as performic, peracetic, perbutyric, pervaleric, perbenzoic, and perphthalic acid. Generally speaking, it is likewise possible to employ alkanoic, cycloalkanoic, aromatic, and heterocyclic peracids in the same manner.

Specific examples of aldehyde hydroperoxides include, aldehyde peracylates, particularly acetaldehyde peracetate, and butyraldehyde perbenzoate.

In general, the preferred organic peroxides are the hydrocarbon hydroperoxides because they are particularly effective as epoxidation agents when reacted with olefins.

As with the organic peroxidic compounds, the inorganic peroxides, of which hydrogen peroxide is a prime example, may be either commercially available products or they may be produced on site for direct utilization in the epoxidation reaction. For example, solutions of hydrogen peroxide in isopropanol are obtained by oxidation of isopropanol with oxygen at elevated temperatures. In this case, the produced solution, after undesirable by-products, such as acetone, are at least partially removed, may be employed in the epoxidation reaction, the isopropanol in this case serving as reaction medium or solvent.

For practical and economic reasons, the most preferred peroxidic compound for use according to the invention is hydrogen peroxide.

In effecting the epoxidation reaction, the alkylene is generally reacted with the peroxidic compound in at least an equivalent amount based on the number of olefinic groups per molecule of alkylene to be oxidized. When the alkylene has only one olefinic bond, then at least an equimolar amount of it is used with the peroxidic compound, e.g., about 1 to about 5 moles, preferably about 1 to about 2 moles, of alkylene per mole of peroxidic compound is used. A proportional increase in the amount of peroxidic compound may be used when diepoxides or triepoxides, rather than monoepoxides, are being prepared.

The alkylene is preferably oxidized in the liquid phase although gaseous alkylene may be employed. When desired, elevated pressures may be used so as to maintain the alkylene material in the liquid phase. Usually, the oxidation is effected in the presence of a solvent which is compatible with and inert to both the alkylene and the peroxidic compound. An organic solvent of a polar nature sufficient to obtain a homogeneous mixture with the alkylene and the peroxidic compound is preferred. The alcohols, especially the secondary alcohols, e.g., isopropanol and sec-butanol, as well as glycols, esters, e.g., isopropyl acetate, linear or cyclic ethers and a few weak carboxylic acids are especially preferred. The organic solvent may be employed in combination with any and/or all of the feedstreams to the epoxidation reactor, i.e., as a solvent for each of the epoxidation reactants. For example, the peroxidic compound may be in solution with part or all of the organic solvent to be employed in the epoxidation reaction. In any event, whether or not all or some of the organic solvent is combined with the peroxidic compound, it is desirable to use about 2 to 100 and preferably about 3 to 20 weight units of organic solvent per weight unit of peroxidic compound. In one embodiment, a peroxidic compound in organic solution may be used having about 1 percent to about 50 percent, preferably about 5 percent to about 30 percent, of peroxidic compound based on the weight of the organic solvent.

In accordance with the invention, the epoxidation reaction is carried out in the presence of an improved molybdenum catalyst. This catalyst is the product of a selective reaction involving an oxygen-containing molybdenum compound, an amine or N-oxide thereof and an alkylene glycol. The oxygen-containing molybdenum compound may be, for example, the ammonium salt of molybdic acid, or it may be one containing only oxygen and molybdenum atoms, e.g., molybdenum dioxide, molybdenum sesquioxide, molybdenum trioxide or mixtures of these. The preferred molybdenum starting material is molybdenum trioxide.

The second reactant used in preparing the catalyst of the invention is an amine or an N-oxide thereof. The amine can be generally represented by the formula

$$R_1R_2R_3N \qquad \qquad I$$

wherein each of $R_1$, $R_2$ and $R_3$ is independently selected from hydrogen, unsubstituted and substituted alkyl of 1–10, preferably 1–6, carbon atoms and unsubstituted and substituted aryl of 6–12, preferably 6–8, carbon atoms; with the proviso that at least one of $R_1$, $R_2$ and $R_3$ is not hydrogen.

The preferred amines of formula I above are those wherein each of $R_1$, $R_2$ and $R_3$ is hydrogen or alkyl, particularly unsubstituted alkyl such as methyl, ethyl, propyl, butyl, pentyl, hexyl and so forth. Especially preferred are the tertiary alkyl amines wherein each alkyl group contains 1–4 carbon atoms. Illustrative of these are trimethylamine, triethylamine, tripropylamine, tributylamine, methyldiethylamine, methyldipropylamine, diethylpropylamine, mixtures thereof and the like. It is to be noted with respect to all of the amines mentioned above that these may be used as such or in the form of N-oxides thereof.

The third reactant is an alkylene glycol. This can be any such compound, or mixture thereof, having 2–10, preferably 2–4, carbon atoms. Illustrative are ethylene glycol, propylene glycol, butylene glycol and so forth. The most preferred glycols are ethylene and propylene glycol and mixtures thereof.

The reactants used in preparing the molybdenum catalyst of the invention may be reacted together in the presence or absence of a solvent. Where a solvent is used, this should be compatible with, but otherwise inert, to the reactants. The alcohols, preferably secondary alcohols such as isopropanol and sec-butanol, are especially suited for this purpose. No criticality is found in the amount of solvent used, if any. But as a practical commercial consideration, about 0 to about 300 or more moles, for example about 1 to about 30 moles, of solvent per mole of molybdenum may be employed.

In the method of making the molybdenum catalysts used in the method of the present invention, the oxygen-containing molybdenum compound, the amine, and the glycol are combined, with or without solvent, and reacted at elevated temperatures. Generally, about 0.1 to about 4 moles, and preferably about 0.5 to about 2 moles, of amine are used per mole of molybdenum; and about 1.5 moles to about 20 moles, and preferably about 1.8 to about 3 moles, of the glycol are employed per mole of molybdenum. These reactants are combined with the oxygen-containing molybdenum compound in any order and heated to an elevated temperature. For example, a temperature of about 70° C. to about 160° C. and preferably about 80° C. to about 150° C., may be used depending upon the particular reactants and solvent employed.

The oxygen-containing molybdenum compound, the amine, and the glycol react to produce a molybdenum catalyst, and the reaction may be run for about 15 minutes or even less to about 12 hours or more depending upon the reactants and the reaction temperature chosen, but generally the reaction is completed to a satisfactory degree in about 0.3 hours to about 3 hours.

Upon completion or substantial completion of the reaction, the catalyst produced is generally in liquid form. In those instances where the catalyst is prepared in the presence of a solvent, it may be separated from the solvent by any known method, e.g., stripping, or it may be used in solution without solvent removal. Thus, whether the catalyst is prepared with or without solvent, the entire reaction product may be effectively used as a catalyst and no separation is necessary. Alternatively, the reaction product may, if desired, be subjected to conventional purification or concentration techniques, e.g., stripping to remove excess reactants, filtration etc.

The novel catalysts obtained are believed to be molybdenum compounds having molybdenum-oxygen central bonding with glycol capping and with amine or ammonium groups possibly attached to molybdenum by ionic or coordination bonds or both. However, this is only based on theoretical speculation and these catalysts are not to be construed as being limited thereto.

The catalysts are used in the method of the invention to promote alkylene epoxidation, and they are soluble in epoxidation media such as those described above. Generally, the catalyst is used in catalytic proportions which of course will vary depending upon the specific catalyst used, the particular alkylene compound or compounds being epoxidized and the reactor design and its flow through characteristics such as residence time. For purposes of illustration only, about 0.01 to about 0.60 of gram-atoms of molybdenum per liter of reaction solution are used. Usually it is desirable to provide about 0.004 to about 0.15 moles, and preferably about 0.008 to about 0.075 moles, of molybdenum per mole of alkylene compound, in the reaction solution, although more catalyst may be used without detrimentally affecting epoxidation.

The alkylene oxidation reaction of the present invention may be performed in a batch operation or it may be a continuous process. It is generally carried out at a temperature ranging from about 0° C. to about 80° C., and preferably about 20° C. Any suitable pressure may be used such as about 1 to about 30, preferably about 10 to about 20 atmospheres. The use of such elevated pressure may be desirable to maintain the reaction mixture in the liquid phase. The oxidation of the alkylene may be satisfactorily completed within a matter of minutes, or it may take days, but usually it is completed within about 5 hours.

During the oxidation reaction, the peroxidic compound gives up an oxygen atom to the alkylene to effect epoxidation. A product mixture of the alkylene oxide, the molybdenum catalyst and undesirable organic by-products is obtained and water may be produced and is produced when $H_2O_2$ is used as the peroxidic compound. Because the water which may be formed enhances the production of undesirable glycols, it is desirable to maintain the amount of water in the reaction mixture at a minimum. When a batch system is employed, the production of undesirable glycol may be mitigated by maintaining the total amount of water present at the end of the reaction below about 20 percent by weight based on the total weight of the reaction mixture. When a continuous system is used, water may be removed from the reaction mixture, if necessary, by removal of a portion of the reactants, separation of the water by evaporation techniques and recycle of the non-aqueous constituents; or alternatively the reaction mixture may have a sufficient amount of solvent so as to produce a low water content product mixture on a continuous basis.

The reaction product containing the desired alkylene oxide obtained by use of the particular molybdenum catalysts of the invention may be subjected to distillation or other purification technique; and the usable constituents, e.g., unreacted alkylene, solvent, etc. and the molybdenum catalyst may be recovered and recycled to the system as desired. The degree of purification of the alkylene oxide product depends upon the ultimate utility of the alkylene oxide and is a matter of choice.

The following examples illustrate the invention. In these examples, all parts and percentages are by weight unless otherwise specified. Examples 1–5 illustrate the preparation of the catalysts of the invention, while Examples 6–8 illustrate the use of the catalysts in alkylene epoxidation.

EXAMPLE 1

To a suitable reactor with a $H_2O$ cooled condenser to prevent removal of volatiles overhead, is charged 1875 g of $MoO_3$ (13.03 mol), 1981 g of propylene glycol (26.06 mol) and 879.1 g of triethylamine (8.69 mol). The reactants are stirred and heated, reflux occurs at about 90° C., but quickly disappears (bp $NEt_3$ 89° C.) and then the reactants are heated to about 130° C. This temperature is maintained for about 0.5 hours. The reaction mixture is then cooled and filtered. No $NEt_3$ odor is detected after reaction completion.

Filtration of material prepared in this manner reveals at most the presence of about 0.6% solids, indicating a solubilization of molybdenum greater than 99%. These solids are determined to contain Mo, C, H, N, O. The greater than 99% conversion is a minimum assuming the solid precipitate is all $MoO_3$ and the presence of the C, H and N suggests an even higher conversion based on the tatol molybdenum present.

The molybdenum catalyst solution is analyzed by NMR and thermal gravimetric analysis (TGA). The TGA analysis yields a weight loss of about 46% at 250° C. and a total weight loss at 700° C. of about 60.5%. These values agree well with the theoretical loss of propylene glycol (41.9%) and the loss of propylene glycol and $NEt_3$ (60.3%).

Elemental analysis is:

|  |  | Theory (%) | Ratio | Experimental (%) | Ratio |
|---|---|---|---|---|---|
|  | Mo | 26.40 | 1.50 | 26.66 | 1.53 |
|  | C | 33.03 | 14.99 | 33.10 | 15.10 |
|  | H | 7.16 | 38.70 | 7.10 | 38.50 |
|  | N | 2.57 | 1 | 2.54 | 1 |
| Kjehldahl | N | 2.57 | 1 | 2.59 | 1 |

In relation to characterization of catalyst obtained, it is estimated that about 20 to 30% of the propylene glycol of the catalyst is coordinated to the molybdenum, with free and coordinated propylene glycol undergoing facile exchange. The exact manner or linkage between the propylene glycol and the molybdenum is not known. The $NEt_3$ is known to be present as $+HNEt_3$ and coordination bonding to the molybdenum is suspected.

The highest ratio of coordinated PG to Mo is Mo/PG=1/0.60; (3.33/2) the lowest 1/0.40 (5/2) (dissolved in 1.6 to 1.4 mols PG). These are analytical limits. The compound could be described as follows:

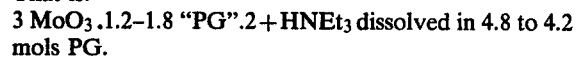

That is:
3 $MoO_3$ .1.2–1.8 "PG".2+$HNEt_3$ dissolved in 4.8 to 4.2 mols PG.

Stability tests show that samples standing for more than 400 days exhibit little or no precipitation or instability.

EXAMPLE 2

In this Example, triethylamine N-oxide is used as the amine reactant. A reactor is charged with 5.00 g (0.03475 mol) $MoO_3$. 12.78 g $Et_3NO.H_2O$ (0.07645 mol $Et_3NO$, i.e., about 70% triethylamine N-oxide) 5.28 g (0.06497 mol) propylene glycol and 15 ml of isopropanol. This suspension is stirred and warmed to reflux (about 83° C.). After about 15 min. at reflux temperature, all the $MoO_3$ is dissolved into the yellow solution which is obtained. The solution is then stripped of isopropanol on a rotary evaporator leaving a brown oil. Conversion of $MoO_3$ into a soluble form of Mo is determined to be about 100%. This product is an effective epoxidation catalyst if used within a short time after preparation. A strong amine odor is evident after about fifteen days of standing, suggesting deterioration at that time.

EXAMPLE 3

A reactor having a heater, reflux condenser and an agitator is charged with 20 g (0.139 moles) of molybdenum trioxide, 112.5 g (1.480 moles) of propylene glycol and 64.5 g (0.499 moles) dibutylamine. The mixture is stirred and heated to 130°–160° C. Agitation is maintained in the temperature range for about 2 hours and then cooled to room temperature. The cooled amber brown colored reaction mixture is filtered or used "as is" for an epoxidation catalyst. Conversion (solubilization Mo): 100%.

EXAMPLE 4

A reactor of the type used in the above Examples is charged with 70.59 g molybdic acid (ammonium salt) (0.417 mol Mo), 63.69 g of propylene glycol (0.834 mole) and 28.13 g $NEt_3$ (0.278 mol). This mixture is stirred and heated at reflux temperature for about seven hours to produce a brownish solution. The suspension is filtered, and cooled, yielding approximately 5 g of a tan solid. The % Mo analysis on the solid indicates that about 94% of the Mo in the molybdic acid is converted by the reaction into a soluble form, the brown oil filtrate. The Mo/N ratio in the brown oil is determined to be about 1.5/1 and the brown oil is found to be a useful epoxidation catalyst.

EXAMPLE 5

A reactor of the type mentioned is charged with 40.00 g $MoO_3$ (0.2780 mol), 28.12 g $NEt_3$ (0.2780 mol), 34.47 g of ethylene glycol (0.556 mol) and 50 ml of isopropanol. The suspension is stirred and heated to reflux and is maintained at reflux for about 1.5 hours to produce a greenish solution. After cooling to room temperature, isopropanol and excess $NEt_3$ (0.09174 mol) is stripped on a rotary evaporator. The greenish solution is then filtered to remove trace solids; % Mo analysis on the solution indicates a solubilization conversion of Mo of about 97%. The final Mo/N ratio in the solution is 3.2/1. Some precipitation occurs upon storage, but the product is found to be an effective epoxidation catalyst.

EXAMPLE 6

A stainless steel pressure vessel is charged with 110 grams of 20% (±2%) solution of total peroxidic compound in isopropanol (a total of 0.582 moles of $H_2O_2$, remainder organic peroxides) and 7.5 grams of the novel molybdenum catalyst prepared by the method of Example 1 (corresponding to 0.021 moles of molybdenum). The pressure vessel is immersed in a 30° C. bath, and 42 grams (1 mole) of liquified propylene is then charged to the sealed pressure vessel at a pressure of about 140 psi. The epoxidation reaction mixture is stirred and maintained at 30° C. for about 4 hours.

Samples of the product mixture are analyzed and found to contain about 10 grams of propylene oxide.

EXAMPLE 7

Example 6 is repeated except that an equimolar amount of butylene is substituted for the propylene, and the reaction is carried out at atmospheric rather than at an elevated pressure. The product mixture is found to contain butylene oxide.

EXAMPLE 8

Example 6 is repeated except that the catalyst of Example 4 is used in place of the Example 6 catalyst. The reaction product mixture is found to contain a substantial amount of propylene oxide.

What is claimed is:

1. A method for preparing an alkylene oxide which comprises reacting an alkylene compound with hydrogen peroxide in the presence of a molybdenum compound catalyst at a reaction temperature ranging from about 20° C. to about 60° C., wherein said catalyst is a preformulated compound prepared by reacting together, at a temperature of about 70°-160° C., (a) an oxygen-containing molybdenum compound selected from the group consisting of molybdenum dioxide, molybdenum sesquioxide, molybdenum trioxide, mixtures of said oxides, and the ammonium salt of molybdic acid, and, per every mole of molybdenum, (b) about 1.5-20 moles of an alkylene glycol having 2-10 carbon atoms and (c) about 0.1-4 moles of an amine or N-oxide thereof, said amine being represented by the formula $R_1R_2R_3N$ in which each of $R_1$, $R_2$, and $R_3$ is independently hydrogen or alkyl of 1-10 carbon atoms with the proviso that at least one of $R_1$, $R_2$ and $R_3$ is not hydrogen.

2. The method of claim 1 wherein said alkylene compound is propylene.

3. The method of claim 1 wherein each of said $R_1$, $R_2$ and $R_3$ is alkyl of 1-4 carbon atoms.

4. The method of claim 3 wherein said oxygen-containing molybdenum compound is selected from the group consisting of molybdenum dioxide, molybdenum sesquioxide, molybdenum trioxide, and a mixture thereof.

5. The method of claim 4 wherein about 1.8-3 moles of said alkylene glycol and about 0.5-2 moles of said amine or its N-oxide are employed per every mole of molybdenum.

6. The method of claim 5 wherein said alkylene glycol contains 2-4 carbon atoms.

7. The method of claim 6 wherein said oxygen-containing molybdenum compound is molybdenum trioxide.

8. The method of claim 7 wherein said alkylene compound is propylene.

9. The method of claim 8 wherein said amine is triethylamine.

10. The method of claim 9 wherein the reaction of said molybdenum trioxide, triethylamine and alkylene glycol is effected at a temperature of about 80°-150° C.

* * * * *

UNITED STATES PATENT AND TRADEMARK OFFICE
CERTIFICATE OF CORRECTION

PATENT NO. : 4,157,346
DATED : June 5, 1979
INVENTOR(S) : Ellwood L. Lines, Robert J. Fairbrother and John A. Herbst It is certified that error appears in the above—identified patent and that said Letters Patent are hereby corrected as shown below:

Column 5, line 3, after "20°C." insert --to about 60°C.--.

Column 5, line 68, "tatol" should be spelled --total--.

Signed and Sealed this

Ninth Day of October 1979

[SEAL]

Attest:

RUTH C. MASON
Attesting Officer

LUTRELLE F. PARKER
Acting Commissioner of Patents and Trademarks